United States Patent [19]

Mizusaki et al.

[11] Patent Number: 4,701,570

[45] Date of Patent: Oct. 20, 1987

[54] ANTITUMOR AGENT

[75] Inventors: Shigenobu Mizusaki, Tokyo; Daisuke Yoshida; Yutaka Saito, both of Kawasaki, all of Japan

[73] Assignee: Japan Tobacco Inc., Tokyo, Japan

[21] Appl. No.: 885,572

[22] PCT Filed: Nov. 1, 1985

[86] PCT No.: PCT/JP85/00609

§ 371 Date: Jul. 2, 1986

§ 102(e) Date: Jul. 2, 1986

[87] PCT Pub. No.: WO86/02835

PCT Pub. Date: May 22, 1986

[30] Foreign Application Priority Data

Nov. 5, 1984 [JP] Japan .................... 59-231391

[51] Int. Cl.$^4$ .................... C07C 35/205
[52] U.S. Cl. .................... 568/821
[58] Field of Search .................... 568/821

[56] References Cited

FOREIGN PATENT DOCUMENTS 2835 5/1986 PCT Int'l Appl. ............ 568/821

OTHER PUBLICATIONS

Roberts et al., "Chemical Abstracts", vol. 55, p553h (1962).
Roberts et al, "J. Organic Chem.", vol. 27, Nov. 1962, pp. 3989–3995.
Fuchs et al., "Chemical Abstracts", vol. 99, pp. 209,808 (1983).
Heemann et al., "Chemical Abstracts", vol. 99, pp. 172,787.
Chemical Abstract 103(19):155572g, Y. Saito et al., Carcinogenesis (London), pp. 1189–1194, 1985.
Chemical Abstract 88(17):116228b (1977).
Chemical Abstract 100(19):k53845n (1984).

*Primary Examiner*—Werren B. Lone
*Attorney, Agent, or Firm*—Schwartz, Jeffery, Schwaab, Mack, Blumenthal & Evans

[57] ABSTRACT

An antitumor agent containing 2,7,11-cembratriene-4,6-diol as an active ingredient, and a process for treatment of tumors with the antitumor agent, are disclosed.

13 Claims, No Drawings

ANTITUMOR AGENT

TECHNICAL FIELD

The present invention relates to an antitumor agent and a process for treatment of tumors, using it.

BACKGROUND ART

Synthetic chemical materials and antibiotics have been employed as low molecular antitumor agents. However, in general, many of these materials are highly toxic and can cause side effects.

The development of an antitumor agent that has low toxicity to normal cells and causes few side effects has therefore been considered desirable.

DISCLOSURE OF INVENTION

It is an object of the present invention to provide an antitumor agent that has superior antitumor effects and that substantially does not show any toxicity to normal cells or display any side effects.

The present invention provides an antitumor agent containing, as an active ingredient, 2,7,11-cembratriene-4,6-diol represented by the following formula:

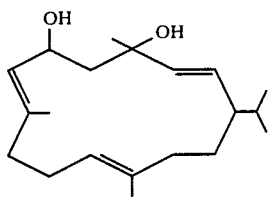

BEST MODE OF CARRYING OUT THE INVENTION

The active ingredient of the antitumor agent according to the present invention is 2,7,11-cembratriene-4,6-diol (hereinafter referred to as CBT) represented by Formula [I] below:

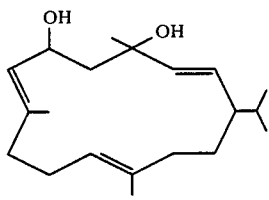

Formula [I]

CBT has two diastereoisomers, i.e., 1S,2E,4S,6R,7E,11E-2,7,11-cembratriene-4,6-diol (hereinafter referred to as α-CBT) represented by Formula [II] below, and 1S,2E,4R,6R,7E,11E-2,7,11-cembratriene-4,6-diol (hereinafter referred to as β-CBT) represented by Formula [III] below. Since both α-CBT and β-CBT show antitumor effects, as will be apparent in Examples which follow, the antitumor agent, according to the present invention, may contain, as an active ingredient, at least one of α-CBT and β-CBT. In this specification and the appended claims, the terms "2,7,11-cembratriene-4,6-diol" and "CBT" mean α-CBT and/or β-CBT. CBT is often represented in a duvatriene form. Accordingly, 4,8,13-duvatriene-1,3-diols, represented by Formulas [IV] and [V] below respectively, are the same compounds as α-CBT and β-CBT. It is to be understood that the compounds represented in the duvatriene form are encompassed within the scope of the present invention.

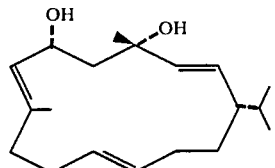

Formula [II]

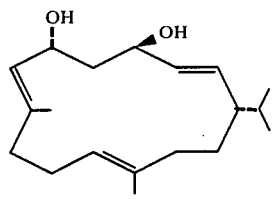

Formula [III]

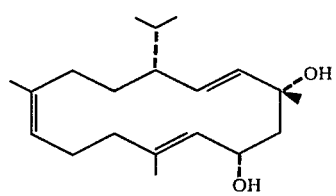

Formula [IV]

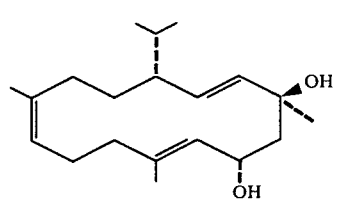

Formula [V]

It is known that CBT is contained in resinous materials on the surface of tobacco leaves. It is also known that CBT is associated with tobacco quality and its flavor during smoking. No pharmacological properties of CBT are known except that it has the effect of preventing the growth of powdery mildew on tobacco (Japanese Patent Disclosure No. 58-157704. In this Disclosure, CBT is represented in the duvatriene form). The present inventors have found for the first time that CBT has an antitumor effect, and the present invention was completed based on this finding.

CBT may be produced, for example, in the following manner: Fresh or dry tobacco leaves are immersed in an organic solvent such as hexane, ether, chloroform, or dichloromethane for a short period of time (for example, 10 seconds to 60 seconds). The immersing temperature is normally between 10° C. and 30° C. The weight ratio of tobacco leaves to the organic solvent is preferably from 2:1 to 1:1. The immersing procedure may be repeated two or more times. The immersion extracts resinous materials found on the surface of the tobacco leaves. This extract is recovered by filtration and is then condensed by evaporating the organic solvent at a reduced pressure and a temperature of 40° C. or lower. The extract is conveniently condensed to a volume of about 1/25 to 1/200 of the original volume.

The condensate is shaken after the addition of a hexane/methanol/water solvent mixture, to transfer CBT to the methanol/water layer. The methanol/water layer is then condensed in the same manner as the extract. The condensate is purified by silica gel chromatography using a hexane/ethyl acetate mixture as an eluting solvent. The removal of the solvent from the eluate at a reduced pressure and a temperature of 40° C. or lower leaves CBT (with a purity of about 80% or higher). The CBT can then be directly used as the active ingredient of an antitumor agent according to the present invention.

The CBT thus obtained may be subjected to high-speed liquid chromatography or alumina column chromatography to separate α-CBT and β-CBT. The elution can be conducted, for example, by means of high-performance liquid chromatography with an acetonitrile/water (70/30) solvent mixture using μBondapak C18 (available from Waters Inc.) as a filler. Then, the α-CBT (retention time: 18 minutes) and β-CBT (retention time: 21 minutes) are eluted separately.

CBT is preferably administered orally, subcutaneously, intravenously, or locally.

The form of administering agent can be any one of the following: powders, granules, tablets, capsules, injectable solutions, local agents, and so on, prepared in a conventional manner by formulation with a pharmacologically acceptable carrier (an excipient such as lactose or starch, or a solvent such as olive oil, soybean oil, or ethanol, for example).

The dose of CBT can be determined according to the patient's symptoms, and the normal dose for an adult is from 1 mg to 100 mg per kg of body weight per day. It can be administered in several installments.

According to the present invention, the antitumor effects of CBT, when administered in the form of an antitumor agent, are believed to accrue from its promoting the return of precancer tissues back to normal cells, or its blocking the conversion of precancer cells to malignant cells, such as is already known from the actions of vitamin A acid and related materials in this regard, or from control over carcinogenesis. Accordingly, CBT exhibits antitumor effects on tissues in the process of cancer formation. CBT is also believed to produce these antitumor effects without inhibiting as much of an immunological reaction as is caused by other anticancer therapies or radiotherapies available today. Also, CBT is believed not to exert any particular influence on the function of normal cells when it controls the proliferation of tumor cells.

EXAMPLE 1

Production of CBT

Ten kilograms of fresh tobacco leaves in the bud-forming stage were immersed in 5 liters of dichloromethane for 30 seconds, and this process was repeated twice to extract resinous materials on the surface of the leaves. The materials which remained insoluble in the dichloromethane extract were removed by filtration, and the extract was condensed at a temperature of 40° C. or lower and at a reduced pressure (20 Torr). The condensate (0.1 liter) was shaken after the addition of 500 ml of methanol, containing 20% by weight of water, and 500 ml of hexane. The resultant methanol layer was recovered and condensed at a temperature of 40° C. or lower and at a reduced pressure (20 Torr). The condensate (40 ml) was then dissolved in 100 ml of a hexane/ethyl acetate (80/20) solvent mixture, and 50 grams of silica gel (Wako Gel C-200) were added thereto. The mixture was then treated at a temperature of 40° C. or lower and at a reduced pressure (20 Torr) to remove the solvent, leaving the silica gel in which crude CBT was adsorbed.

The silica gel thus obtained was then placed on silica gel (Wako Gel C-200) filled in a column (inner diameter: 5 cm; height: 85 cm) and subjected to elution with a hexane, and then with a hexane/ethyl acetate (70/30) solvent mixture. A total of 4 liters of eluate was recovered from the hexane/ethyl acetate solvent mixture. This eluate was condensed at a temperature of 40° C. or lower and at a reduced pressure (20 Torr) to thoroughly remove the solvent, leaving 13 grams of CBT, with an 80% purity.

A 0.5 gram portion of CBT was dissolved in an acetonitrile/water (60/40) solvent mixture and was then subjected to elution with an acetonitrile/water (70/30) solvent mixture by means of high-speed liquid chromatography (Model LC-5A available from Shimazu Seisakusho) using μBondapak C18 as a filler to separate α-CBT (retention time: 18 minutes) and β-CBT (retention time: 21 minutes). Six grams of barely crystallizable α-CBT and 2 grams of crystalline β-CBT were thus obtained.

| Analysis of α-CBT | |
| --- | --- |
| Melting point: | 65–66° C. |
| Specific optical rotation: | $[\alpha]_D^{25} + 281.6°$ C. (chloroform) |
| Infrared spectrum: | 3300(S), 1665(W), 1345, 1190, 1160, 1118, 1024, 995, 974(S), 954, 818 cm$^{-1}$ |
| Ultraviolet spectrum: | $\lambda_{max}^{ethanol}$ - 220 nm |
| $^1$H-NMR spectrum (500 MHz): | $\delta_{TMS}^{CDCl_3}$ ppm; 0.79(d, J = 6.7 Hz, 3H), 0.83(d, J = 6.7 Hz, 3H) 1.34(S, 3H), 1.52(d, J = 1.0 Hz, 3H) 1.67(d, J = 1.3 Hz, 3H), 4.48(ddd, J = 2.0, 8.7 Hz, 1H), 5.04(bt, J = 5.0 Hz, 1H), 5.33(3H) |
| Mass spectrum: | (70 eV) m/Z (%) 43(100), 55(42), 81(69), 95(30), 121(18), 189(4), 245(4), 288(0.1), 306(M$^+$, 0.1) |
| Analysis of β-CBT | |
| Melting point: | 127–127.5° C. |
| Specific optical rotation: | $[\alpha]_D^{25} + 162°$ (chloroform) |
| Infrared spectrum: | 3280(S), 1667(W), 1166, 1142, 1117, 1095, 1083, 1035, 975(S), 946, 923, 889, 875 cm$^{-1}$ |
| Ultraviolet spectrum: | $\lambda_{max}^{ethanol} = 220$ nm |
| $^1$H-NMR spectrum (500 MHz): | $\delta_{TMS}^{CDCl_3}$ ppm, 0.80(d, J = 6.7 Hz, 3H), 0.83(d, J = 6.7 Hz, 3H) 1.40(S, 3H), 1.51(bs, 3H), 1.70(d, J = 1.0 Hz, 3H), 1.86(dd, J = 9.0, 14.1 Hz, 1H), 2.05(dd, J = 1.3, 14.1 Hz, 1H), 4.81(ddd, J = 1.3, 9.0, 9.4 Hz, 1H) 5.00(bt, J = 5.4 Hz, 1H), 5.22(dd, J = 9.0, 15.4 Hz, 1H), 5.26(bd, J = 9.4 Hz, 1H), 5.40(d, J = 15.4 Hz, 1H) |
| Mass spectrum: | (70 eV) m/Z (%) 43(100), 55(59), 81(95), 95(50), 121(35), 177(5), 245(8), 306(M$^+$, 0.1) |

EXAMPLE 2

Antitumor Effects of CBT

A group of 6-week-old female ICR-JCL mice was inoculated, intraperitoneally, with a suspension of Sarcoma 180 cells at a dose of 0.25 ml per mouse, and proliferated cancer cells were removed one week after inoculation. The cancer cells were transplanted at a dose of $1 \times 10^6$ cells per mouse to another 7 groups (each group consisting of 10 mice) of female ICR-JCL mice by subcutaneous injection in the hollow of one front leg. α-CBT and β-CBT prepared in Example 1 above were each formulated into an antitumor agent by dissolving them in olive oil to a concentration of 0.15 to 1.5% by weight. The antitumor agent was administered to the mice every second day for a total of ten doses, starting 24 hours after transplantation of the cancer cells. The antitumor agent was administered to the first to sixth groups of mice in the CBT concentrations per dose listed in Table 1 below, and the seventh group of mice, used as a control group, was administered only olive oil in a total amount of 6,700 mg/kg. Tumor tubercles formed were removed 24 hours after the tenth dose, and the tumor control rate was calculated by the following formula:

$$\{1-(B/A)\} \times 100(\%)$$

in which A is an average tumor weight in the control group, and B is an average tumor weight in each of the groups to which CBT was administered. The results are shown in Table 1.

TABLE 1

| Antitumor Effect of CBT on Sarcoma 180 | | | | | | |
|---|---|---|---|---|---|---|
| Compound | α-CBT | | | β-CBT | | |
| Dose (mg/kg) | 10 | 50 | 100 | 10 | 50 | 100 |
| Tumor Control Rate (%) | 25 | 48 | 67 | 22 | 46 | 64 |

As is apparent from Table 1, both α-CBT and β-CBT show dose-dependent antitumor effects on Sarcoma 180.

EXAMPLE 3

Effects on Control of Tumor Formation

The fur on the backs of 7-week-old female ICR-JCL mice was shaved to expose the skin, and 0.1 ml of an acetone solution containing 100 μg of dimethylbenzoanthracene (DMBA) was applied to the exposed site. Thereafter, 0.1 ml of an acetone solution containing 0.5 μg of 12-O-tetradecanoylphorbol-13-acetate (TPA) was applied to the site at a rate of twice a week for 25 weeks, starting 1 week after the application of DMBA. In order to investigate the effct of CBT on control of tumor formation, an acetone solution containing 1 mg of α-CBT or β-CBT was applied to the site 40 minutes prior to every TPA application. The formation of tumors was observed after 25 weeks for each group of mice, including a control group to which only TPA but not CBT was applied. Each group consisted of 30 mice. The tumor formation control rate was calibrated by the following formula:

$$\{1-(C/D)\} \times 100(\%)$$

in which C is the number of tumors formed in the group of mice to which only TPA was applied, and D is the number of tumors formed in the group of mice to which CBT was applied before the application of TPA. C and D were observed with the naked eye. The results are shown in Table 2.

TABLE 2

| Effect of CBT on Control of Tumor Formation by TPA | |
|---|---|
| Compound | Tumor Formation Control Rate (%) |
| α-CBT | 80 |
| β-CBT | 65 |

As is apparent from Table 2, α-CBT and β-CBT both showed remarkable control effects on tumor formation.

EXAMPLE 4

Toxicity (1) Acute toxicity tests

The acute toxicity of CBT was investigated by intraperitoneal or oral administration thereof to 6-week-old ICR-JCL mice and Wistar JCL rats. A solution of α-CBT or β-CBT in olive oil was intraperitoneally injected, or was administered to the animals through an oral probe. The number of animals tested for each method of administration was 10. After administration, observation was continued while the animals were fed normally for 7 days. The animals were killed on the eighth day to allow macroscopic observations, and $LD_{50}$ values were calculated according to the Richfield-Wilcockson method.

The anatomical observations showed no abnormalities. The $LD_{50}$ values obtained are shown in Table 3.

TABLE 3

| Acute Toxicity Tests ($LD_{50}$ Values) | | | |
|---|---|---|---|
| | | $LD_{50}$ (mg/kg) | |
| Animal | Compound | Intraperitoneal Administration | Oral Administration |
| Mouse | α-CBT | 3000 | 4200 |
| | β-CBT | 3000 | 4000 |
| Rat | α-CBT | 3200 | 4100 |
| | β-CBT | 3100 | 3800 |

As is apparent from Table 3, the $LD_{50}$ values of CBT in both the mice and rats were higher than 3 grams per kilogram. CBT was therefore found to have a high degree of safety, since it belongs to the "very weak toxicity" category according to the Lumis classification.

(2) Subacute toxicity tests

A solution of α-CBT or β-CBT was orally administered to 6-week-old ICR-JCL mice through a probe every day for 20 days in a row, in a dose of 100 mg/kg. Only olive oil was administered to each mouse in a control group in a dose of 6,700 mg/kg. Each group consisted of 10 mice. The mice were killed 24 hours after the last dose to allow hematological examinations, anatomical observations, weighing of major organs, and pathohistological examinations. The results are shown in Tables 4 and 5.

TABLE 4

| | Hematological Examinations | | | | |
|---|---|---|---|---|---|
| Compound | Number of Leukocytes (cells/mm) | Number of Erythrocytes (cells/mm) | Amount of Hb (g/dl) | Hematocrit Value | GOT (mV/ml) |
| α-CBT | 6300 | $6.1 \times 10^6$ | 14.7 | 35% | 52 |
| β-CBT | 6350 | $6.0 \times 10^6$ | 14.5 | 35% | 51 |

TABLE 4-continued

| | Hematological Examinations | | | | |
|---|---|---|---|---|---|
| Compound | Number of Leukocytes (cells/mm) | Number of Erythrocytes (cells/mm) | Amount of Hb (g/dl) | Hematocrit Value | GOT (mV/ml) |
| Control | 6300 | $6.0 \times 10^6$ | 14.6 | 35% | 53 |

TABLE 5

| | Weights of Major Organs (g) | | | | |
|---|---|---|---|---|---|
| Compound | Liver | Spleen | Left Kidney | Right Kidney | Heart |
| α-CBT | 1.47 | 0.10 | 0.18 | 0.19 | 1.21 |
| β-CBT | 1.48 | 0.11 | 0.18 | 0.19 | 1.20 |
| Control | 1.49 | 0.11 | 0.18 | 0.19 | 1.20 |

As shown in Tables 4 and 5, the administration of CBT did not cause any abnormalities in the hematological profile or organ weights. In addition, no abnormalities were found in body weight increase, amount of feed intake, macroscopic anatomical observations, or pathohistological examinations (by means of an optical microscope).

(3) Mutagenesis tests

The mutagenesis test was conducted according to the Ames method (Mutation Research, Vol. 113, 1983, p. 173) with the use of 4 strains of *Salmonella typhimurium*: TA1535, TA1537, TA98, and TA100.

0.1 ml of a Salmonella suspension (number of bacteria: $2 \times 10^8$), 0.5 ml of an S9 mix (prepared by adding nicotine adenine dinucleotide, in an amount of 3.2%, to a supernatant obtained by centrifuging rat liver homogenates at 9,000 G) or 0.5 ml of a phosphate buffer (pH 7.4), and 0.1 ml of a dimethylsulfoxide solution of α-CBT or β-CBT were added, in that order, to 2 ml of soft agar (containing 0.05 mM of histidine or biotin) heated to 40° C. After stirring, the mixture was cast on agar plates. The agar plates were incubated at 37° C. for 2 days, and colonies formed thereon were counted as the number of reverse mutants.

Tables 6 and 7 respectively show the results when S9 mix was added and when S9 mix was not added.

TABLE 6

| | Mutagenesis Tests (S9 mix added) | | | | |
|---|---|---|---|---|---|
| | Amount | Number of Reverse Mutants | | | |
| Compound | μg | TA1535 | TA1537 | TA98 | TA100 |
| α-CBT | 0 | 23 | 7 | 45 | 129 |
| | 100 | 20 | 8 | 46 | 129 |
| | 500 | 23 | 7 | 43 | 125 |
| | 1000 | 21 | 6 | 41 | 120 |
| β-CBT | 0 | 23 | 7 | 45 | 129 |
| | 100 | 19 | 7 | 47 | 108 |
| | 500 | 17 | 9 | 48 | 130 |
| | 1000 | 18 | 8 | 43 | 126 |

TABLE 7

| | Mutagenesis Tests (No S9 mix added) | | | | |
|---|---|---|---|---|---|
| | Amount | Number of Reverse Mutants | | | |
| Compound | μg | TA1535 | TA1537 | TA98 | TA100 |
| α-CBT | 0 | 15 | 9 | 47 | 100 |
| | 100 | 16 | 7 | 45 | 101 |
| | 500 | 16 | 8 | 50 | 108 |
| | 1000 | 17 | 7 | 43 | 98 |
| β-CBT | 0 | 15 | 9 | 47 | 100 |
| | 100 | 15 | 7 | 48 | 100 |
| | 500 | 14 | 7 | 49 | 101 |
| | 1000 | 16 | 7 | 49 | 103 |

Tables 6 and 7 demonstrate that α-CBT and β-CBT are highly safe compounds which substantially do not induce the reverse mutation of Salmonella strains in either case of adding S9 mix or of not adding S9 mix.

We claim:

1. An antitumor agent comprising, as an active ingredient, 2,7,11-cembratriene-4,6-diol represented by the formula:

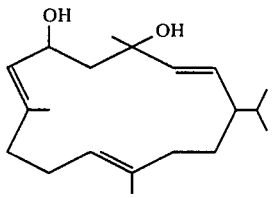

and a pharmacologically acceptable carrier for said active ingredient, such that said active ingredient is provided to a subject in orally, subcutaneously, intravenously or locally administrable form, wherein said active ingredient is present in an amount sufficient to provide a dose of 1 to 100 mg per kg of subject body weight per day.

2. An antitumor agent according to claim 1, in which the active ingredient is 1S,2E,4S,6R,7E,11E-2,7,11-cembratriene-4,6,-diol.

3. An antitumor agent according to claim 1, in which the active ingredient is 1S,2E,4R,6R,7E,11E-2,7,11-cembratriene-4,6-diol.

4. An antitumor agent according to claim 1, in which the active ingredient is a mixture of 1S,2E,4S,6R-,7E,11E-2,7,11-cembratriene-4,6-diol and 1S,2E,4R,6R,7E-2,7,11-cembratriene-4,6-diol.

5. Use, for treatment of tumors, of 2,7,11-cembratriene-4,6-diol represented by the formula:

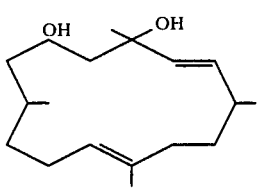

in combination with a pharmacologically acceptable carrier, such that said active ingtredient is provided to a subject in orally, subcutaneously, intravenously or locally administrable form, wherein said active ingredient is used in an amount sufficient to provide a dose of 1 to 100 mg per kg of subject body weight per day.

6. Use, according to claim 5, of 1S,2E,4S,6R,7E,11E-2,7,11-cembratriene-4,6-diol for treatment of tumors.

7. Use, according to claim 5, of 1S,2E,4R,6R,7E,11E-2,7,11-cembratriene-4,6-diol for treatment of tumors.

8. Use, for treatment of tumors according to claim 5, of a mixture of 1S,2E,4S,6R,7E,11E-2,7,11-cembratriene-4,6-diol and 1S,2E,4R,6R,7E,11E-2,7,11-cembratriene-4,6-diol.

9. A process for treatment of tumors in humans, comprising the step of administering to a subject an antitumor agent which contains, as an active ingredient, an antitumor-effective amount of 2,7,11-cembratriene-4,6-diol represented by the formula:

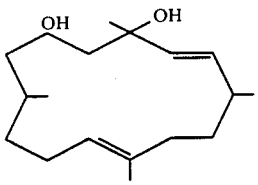

and a pharmacologically acceptable carrier for said active ingredient, such that said active ingredient is provided in orally, subcutaneously, intravenously or locally administrable form.

10. A process according to claim 9, in which the active ingredient is 1S,2E,4S,6R,-7E,11E-2,7,11-cembratriene-4,6-diol.

11. A process according to claim 9, in which the active ingredient is 1S,2E,4R,6R,7E,11E-2,7,11-cembratriene-4,6-diol.

12. A process according to claim 9, in which the active ingredient is a mixture of 1S,2E,4S,6R,7E,11E-2,7,11-cembratriene-4,6-diol and 1S,2E,4R,6R,7E,11E-2,7,11-cembratriene-4,6-diol.

13. A process according to claim 9, in which the active ingredient is administered at a dose of 1 to 100 mg per kg of subject body weight per day.

* * * * *